(12) United States Patent
Flitcroft

(10) Patent No.: US 12,349,973 B2
(45) Date of Patent: Jul. 8, 2025

(54) SYSTEM FOR AND METHOD OF MONITORING EYE MEDICATION

(71) Applicant: Ocuvation Limited, Dublin (IE)

(72) Inventor: Ian Flitcroft, Dublin (IE)

(73) Assignee: OCUVATION LIMITED, Dublin (IE)

( * ) Notice: Subject to any disclaimer, the term of this patent is extended or adjusted under 35 U.S.C. 154(b) by 0 days.

(21) Appl. No.: 17/767,530

(22) PCT Filed: Oct. 12, 2020

(86) PCT No.: PCT/EP2020/078652
§ 371 (c)(1),
(2) Date: Apr. 8, 2022

(87) PCT Pub. No.: WO2021/069750
PCT Pub. Date: Apr. 15, 2021

(65) Prior Publication Data
US 2024/0065545 A1    Feb. 29, 2024

(30) Foreign Application Priority Data

Oct. 11, 2019 (GB) ...................................... 1914758

(51) Int. Cl.
*A61B 3/11* (2006.01)
*A61B 3/09* (2006.01)
(Continued)

(52) U.S. Cl.
CPC ................ *A61B 3/112* (2013.01); *A61B 3/09* (2013.01); *A61B 5/4839* (2013.01);
(Continued)

(58) Field of Classification Search
CPC ......... A61B 3/112; A61B 3/09; A61B 5/4839; A61B 5/4848; A61B 5/163; A61F 9/0008;
(Continued)

(56) References Cited

U.S. PATENT DOCUMENTS 10,390,802 B1 *  8/2019  Picard .................... A61B 3/113
2014/0257206 A1 *  9/2014  Fateh .................... A61F 9/0017
                                                                    604/290
(Continued)

FOREIGN PATENT DOCUMENTS

EP        2799009 A1    11/2014
WO     86/04799 A1     8/1986
(Continued)

OTHER PUBLICATIONS

Chia, A, et al., "Atropine for the Treatment of Childhood Myopia: Safety and Efficacy of 0.5%, 0.1 %, and 0.01 % Doses (Atropine for the Treatment of Myopia 2)," Ophthalmology, 119(2):347-354 (2012).
(Continued)

*Primary Examiner* — Mohammed A Hasan
(74) *Attorney, Agent, or Firm* — Hamilton, Brook, Smith & Reynolds, P.C.

(57) ABSTRACT

A system for and method of monitoring/measuring the level of receptoral action/blockade and intra-ocular penetration/concentration of an eye medication and determining an optimal treatment regime based on the level of receptoral action/blockade and intra-ocular penetration/concentration of the eye medication.

14 Claims, 9 Drawing Sheets

(51) Int. Cl.
*A61B 5/00* (2006.01)
*A61F 9/00* (2006.01)
*A61K 31/222* (2006.01)
*A61K 31/439* (2006.01)

(52) U.S. Cl.
CPC .......... *A61B 5/4848* (2013.01); *A61F 9/0008* (2013.01); *A61K 31/222* (2013.01); *A61K 31/439* (2013.01)

(58) Field of Classification Search
CPC ..... A61K 31/222; A61K 31/439; A61P 27/10; A61P 27/02
USPC .......................................................... 351/246
See application file for complete search history.

(56) References Cited

U.S. PATENT DOCUMENTS

| | | | | |
|---|---|---|---|---|
| 2016/0338947 | A1* | 11/2016 | Leahy | A61K 47/32 |
| 2018/0177453 | A1* | 6/2018 | Jardeleza | A61J 7/0481 |
| 2019/0191995 | A1 | 6/2019 | Giovinazzo | |

FOREIGN PATENT DOCUMENTS

| | | | |
|---|---|---|---|
| WO | 198604799 | A1 | 8/1986 |
| WO | 2011016029 | A2 | 2/2011 |
| WO | 2021069750 | A1 | 4/2021 |

OTHER PUBLICATIONS

Dabisch, Paul A., et al., "2007 Toxicological Sciences," 100(1):281-289 (2007).

Huang, J., et al., "Efficacy Comparison of 16 Interventions for Myopia Control in Children: A Network Meta-analysis," Ophthalmology, 123(4):697-708 (2016).

Lanchulev, T., et al., "High-precision piezo-ejection ocular microdosing: Phase II study on local and systemic effects of topical phenylephrine," Therapeutic Delivery, 9(1):17-27 (2018).

Loughman, J., & Flitcroft, D.I., "The acceptability and visual impact of 0.01% atropine in a Caucasian population," British Journal of Ophthalmology, 100(11):1525-1529 (2016).

Yam, J., et al., "Low-Concentration Atropine for Myopia Progression (LAMP) Study: A Randomized, Double-Blinded, Placebo-Controlled Trial of 0.05%, 0.025%, and 0.01% Atropine Eye Drops in Myopia Control," Ophthalmology, 126(1):113-124 (2019). (Abstract).

International Search Report and Written Opinion issued for International Application No. PCT/EP2020/078652, entitled "A System for and Method of Monitoring Eye Medication," mailed on Jan. 26, 2021.

John V. Lovasik*, Pharmacokinetics of Topically Applied Cyclopentolate HCl and Tropicamide, May 14, 1986, American ,Journal of Optometry & Physiological Optics, 787-803, vol. 63, No. 10.

Jon E. Wold, Subjective and objective measurement of human accommodative amplitude, Jul. 16, 2003, J Cataract Refract Surg, 1878-1888, 29.

* cited by examiner

SYSTEM FOR AND METHOD OF MONITORING EYE MEDICATION

This application is the U.S. National Stage of International Application No. PCT/EP2020/078652, filed Oct. 12, 2020, which designates the U.S., published in English, and claims priority under 35 U.S.C. § 119 or 365 (c) to Great Britain Application No. 1914758.6, filed Oct. 11, 2019. The entire teachings of the above applications are incorporated herein by reference.

INTRODUCTION

This disclosure generally relates to a system for and method of monitoring/measuring the level of receptoral action/blockade and intra-ocular penetration/concentration of an eye medication and determining an optimal treatment regime based on the level of receptoral action/blockade and intra-ocular penetration/concentration of the eye medication. More particularly, the disclosure relates to a system for and method of monitoring/measuring the level of receptoral action/blockade and intra-ocular penetration/concentration of anti-muscarinic medications and determining an optimal myopia treatment regime based on the level of receptoral action/blockade and intra-ocular penetration/concentration of the anti-muscarinic medication.

BACKGROUND

Application of the anti-muscarinic eye medication atropine to the eye in eye drops with a concentration of 0.5%-1.0% is the most effective treatment discovered to date to prevent myopia progression (Huang, J., Wen, D., Wang, Q., McAlinden, C., Flitcroft, I., Chen, H., . . . Qu, J. (2016). Efficacy comparison of 16 interventions for myopia control in children: A network meta-analysis. Ophthalmology, 123 (4), 697-708). Studies in Singapore first published in 2012 (ATOM2 Study, Chia, A., Chua, W.-H., Cheung, Y.-B., Wong, W.-L., Lingham, A., Fong, A., & Tan, D. (2012). Atropine for the Treatment of Childhood Myopia: Safety and Efficacy of 0.5%, 0.1%, and 0.01% Doses (Atropine for the Treatment of Myopia 2). Ophthalmology, 119(2), 347-354) demonstrated that very low doses of atropine, 0.01%, applied to an eye in the form of eye drops was almost as effective at slowing down the progression of myopia as standard doses (1.0%). The interest in low dose atropine is that atropine at standard doses causes pupil dilatation and paralysis of accommodation (near-focusing) by antagonism of muscarinic receptors within the eye that can last up to 7 days. These effects on the pupil and the accommodation system are the primary uses of atropine, but in relation to treatment of myopia progression these can be regarded as side-effects which have limited its use in myopia control. At 0.01% the side effects on pupil size and accommodation are minimal and certainly easily tolerated by most subjects (Loughman, J., & Flitcroft, D. I. (2016). The acceptability and visual impact of 0.01% atropine in a Caucasian population. British Journal of Ophthalmology, 100(11), 1525-1529), but this concentration has proved effective in slowing myopia progression in the longest clinical trial to date of low dose atropine (the ATOM2 study).

This has led to great interest in using 0.01% atropine eye drops as a treatment to prevent myopia progression. There is also a debate as to whether 0.01% atropine is truly effective as some subsequent studies (e.g. the LAMP study in Hong Kong, Yam, J. C., Jiang, Y., Tang, S. M., Law, A. K. P., Chan, J. J., Wong, E., . . . Pang, C. P. (2019). Low-Concentration Atropine for Myopia Progression (LAMP) Study: A Randomized, Double-Blinded, Placebo-Controlled Trial of 0.05%, 0.025%, and 0.01% Atropine Eye Drops in Myopia Control. Ophthalmology, 126(1), 113-124) have found minimal effects on eye growth. These same studies have also found minimal side effects at the lowest doses, with increasing effectiveness and increasing side effects with increasing concentrations of atropine.

One challenge with atropine preparations is that atropine is not very stable in solution at physiological levels of pH (i.e. close to 7.0). This leads to the possibility that a preparation may not be stable and hence the relative lack of effectiveness of a given preparation may be due to loss of active drug over time. The other challenge with such low doses is that variability of penetration into the eye, where the drug exerts its effects, may influence effectiveness. In addition, atropine and other antimuscarinic drugs are bound by the pigment melanin which is present in variable amounts in eyes of different colour, and this can affect the amount of drug that reach the anti-muscarinic receptors. These variable factors mean that in subjects that have no side effects, it is possible that an ineffective amount of drug is reaching the receptors. In such cases, a higher concentration or more frequent application would be appropriate to ensure a therapeutically effective dose in being achieved within the eye.

For most ocular applications of topical drugs, and when atropine is used to dilate pupils, the intent is to achieve maximal blockade of the target receptors to achieve maximal effectiveness. In the case of low doses of atropine (e.g. in the range 0.01% to 0.1%), achieving an acceptably low level of side effects, in terms of photophobia (generated by increased pupil size) and loss of an ability to read up close (generated by loss of accommodation), requires only partial blockade of the receptors in question.

Both pupil size and accommodation are controlled by feedback loops, whereby a change in light levels reaching the retina or a retinal blur signal leads to a response in the eye which serves to reduce the imposed change in light levels by changing pupil size or minimise retinal blur by changing the focusing distance of the eye.

However, existing technology only allows for measurement of pupil size and level of accommodation of an eye both in terms of static measurements and dynamic measurements as it is not acceptable to take a sample from a living eye to measure drug levels in the eye due to risks of infection etc. Accordingly, the known techniques can simply measure the overall response from the pupillary light and accommodation control systems and do not attempt to determine or estimate the internal factors such as the degree to which the effector muscles in the pupil and ciliary body are operating. Pupil size can be measured by infra-red pupillometry whereby infra-red light is shone into the eye and the amount of light reflected back through the pupil is measured to determine pupil area and hence diameter. For example, WO 2011/016029 A2 describes a conventional pupillometer for performing visual field tests on individuals. Pupillometry can also be achieved by image analysis of high-speed video of the front of the eye.

Accommodation can also be measured dynamically with accommodation measurement devices e.g. with systems based on the Sheiner principle, retinoscopic systems, retinal image best-focus or ray deflection principle. Accommodative convergence can be measured with devices that determine eye position and the direction of gaze (e.g. Maddox wing, limbal eye trackers or video eye trackers). The accommodative convergence ratio (AC/A) can determined from the ratio of this accommodative convergence response to the accommodative stimulus or accommodative response.

However, the existing devices to measure pupil size and accommodation are only configured to monitor the functions of these in relation to either normal function or in the presence of disease rather than being optimised to monitor the level of muscarinic receptor blockade or level of intra-ocular penetration/concentration of anti-muscarinic medications to determine optimal myopia treatment regimes in patients.

In short, the current techniques of measuring pupil size and accommodation measure just the end result of two complex feedback loops while the action of the feedback loops masks the effect of partial receptoral blockade of the type that needs to be monitored when employing medications such as anti-muscarinic medications. Most antagonistic drugs act in a competitive manner, i.e. their blocking action is a function of both the concentration of the drug and the agonist, which may often be a physiological neurotransmitter. The term receptoral blockade, in this context, therefore means the degree to which the antagonistic drug blocks the physiological function within the eye, which in turn affects, in a more complex and nonlinear manner, the operation of the neurological pupil or accommodation or accommodative convergence control systems that operate within the brain. In addition, since the effects of atropine on eye growth can take a year or more to determine, and the rapidly apparent side effects of low dose atropine only present in a small proportion of subjects, this raises the need for measurement devices and techniques to determine how much atropine is reaching muscarinic receptors within the eye.

In summary, while current devices and methods measure pupil size and accommodation, they are not configured to and, moreover, fail to extract the appropriate parameters to best estimate the degree of receptoral blockade in the pupil or ciliary muscle resulting from the application of antimuscarinic preparations such as atropine and related drugs. The known devices and method are also not adapted to process such parameters in a manner that facilitates the measurement of the intra-ocular penetration/concentration of an anti-muscarinic medication and nor are the known devices or methods capable of determining an optimal myopia treatment regime based on the level of receptoral action and intra-ocular penetration/concentration of the anti-muscarinic medication.

It is therefore an object to overcome at least some of the problems of the prior art.

SUMMARY

According to the invention there is provided a method and system, as set out in the appended claims, for monitoring the level of intra-ocular concentration of an eye medication in a patient comprising:
- a testing device for testing pupil response or accommodation response to the eye medication, said device configured to test the patient to extract data on the pupil response or accommodation response, and the system is configured to:
- estimate the intraocular concentration of the medication based on the extracted data.

Preferably, the intraocular concentration is estimated by computing at least one data parameter value and comparing with a reference database of known data parameters.

Advantageously, at least one data parameter is calculated from an open loop phase of the pupil or accommodation response.

Preferably, the at least one data parameter comprises maximal change in pupil diameter from baseline, size change at 2× latency time, pupil velocity at 2× latency time, average velocity up to 2× latency time, peak velocity up to and including 2× latency time point and area under curve at 2LP.

Alternatively or in addition, the at least one data parameter comprises an accommodation or accommodative convergence parameter.

Preferably, a level of receptoral blockade caused by the eye medication is estimated by comparing the at least one data parameter with a reference database comprising a pre-treatment patient baseline.

Alternatively, a level of receptoral blockade caused by the eye medication is estimated by comparing the at least one data parameter with a reference database comprising a normative database or reference group data.

Preferably, the level of intra-ocular concentration of the eye medication is calculated from the estimated level of receptoral blockade.

Advantageously, the system further comprises the step of determining an optimal treatment regime based on the intra-ocular concentration of the eye medication.

Suitably, the system comprises the step of assessing whether the calculated intra-ocular concentration is in a therapeutic range.

Additionally, the system comprises determining a ratio of the calculated intra-ocular concentration to a desired intra-ocular concentration and calculating a dose or dosing frequency accordingly and subsequently comprises the step of adjusting the dose as required.

In a preferred embodiment, the medication is an anti-muscarinic medication. Preferably, the anti-muscarinic medication is selected from the group consisting of atropine, homatropine, cyclopentolate, tropicamide, hyoscyamine and scopolamine. Optionally, the treatment regime is a myopia treatment regime.

In one embodiment, the testing device comprises a pupillometer. Preferably, the pupillometer comprises:
- a stimulation/testing chamber;
- a short wavelength visible light source, and a
- long wavelength light source wherein the long wavelength light source is configured to be actuatable for a duration less than or equal to the latency of eye pupil response.

Suitably, the pupillometer comprises a step or impulse function to actuate the long wavelength light source for a duration less than or equal to the latency of eye pupil response.

Advantageously, the short wavelength visible light source is configured to be permanently on during monitoring.

In another embodiment, the testing device comprises an accommodation or accommodative convergence measurement device.

Preferably, the testing device comprises a controller to control and record stimulus control, data capture, storage and analysis functions. Advantageously, the controller comprises a computer.

The invention also extends to a method of monitoring the level of intra-ocular concentration of an eye medication in a patient comprising testing the patient with a testing device to extract data on the pupil response or accommodation response and estimating the intraocular concentration of the medication based on the extracted data.

Suitably, the intraocular concentration is estimated by computing at least one data parameter value and comparing with a reference database of known data parameters.

Preferably, at least one data parameter is calculated from an open loop phase of the pupil or accommodation response. In one embodiment, the at least one data parameter comprises maximal change in pupil diameter from baseline, size change at 2× latency time, pupil velocity at 2× latency time, average velocity up to 2× latency time, peak velocity up to and including 2× latency time point and area under curve at 2LP.

Alternatively, the at least one data parameter comprises an accommodation or accommodative convergence parameter.

Preferably, a level of receptoral blockade caused by the eye medication is estimated by comparing the at least one data parameter with a reference database comprising a pre-treatment patient baseline.

Alternatively or in addition, a level of receptoral blockade caused by the eye medication is estimated by comparing the at least one data parameter with a reference database comprising a normative database or reference group data.

Preferably, the level of intra-ocular concentration of the eye medication is calculated from the estimated level of receptoral blockade.

Suitably, the method further comprises the step of determining an optimal treatment regime based on the intra-ocular concentration of the eye medication.

Advantageously, the method comprises assessing whether the calculated intra-ocular concentration is in a therapeutic range.

Preferably, the method comprises determining a ratio of the calculated intra-ocular concentration to a desired intra-ocular concentration and calculating a dose or dosing frequency accordingly.

Suitably, the method further comprises the step of adjusting the dose as required.

In a preferred embodiment of the method of the invention, the medication is an anti-muscarinic medication.

Preferably, the anti-muscarinic medication is selected from the group consisting of atropine, homatropine, cyclopentolate, tropicamide, hyoscyamine and scopolamine.

Optionally, the treatment regime is a myopia treatment regime.

In one embodiment, the method further comprises the step of smoothing data with a filter.

In another embodiment, the invention further comprises the step of machine learning from the data obtained from patients.

In another embodiment, the invention also extends to a computer implemented method of treating a patient with an eye medication comprising:
  testing the patient with a testing device to extract data on the pupil response or accommodation response, and
  estimating the intraocular concentration of the medication based on the extracted data to monitor the level of intra-ocular concentration of the eye medication in the patient.

Suitably, the intraocular concentration is estimated by computing at least one data parameter value and comparing with a reference database of known data parameters.

Preferably, at least one data parameter is calculated from an open loop phase of the pupil or accommodation response. In one embodiment, the at least one data parameter comprises maximal change in pupil diameter from baseline, size change at 2× latency time, pupil velocity at 2× latency time, average velocity up to 2× latency time, peak velocity up to and including 2× latency time point and area under curve at 2LP.

Alternatively, the at least one data parameter comprises an accommodation or accommodative convergence parameter.

Preferably, a level of receptoral blockade caused by the eye medication is estimated by comparing the at least one data parameter with a reference database comprising a pre-treatment patient baseline.

Alternatively or in addition, a level of receptoral blockade caused by the eye medication is estimated by comparing the at least one data parameter with a reference database comprising a normative database or reference group data.

Preferably, the level of intra-ocular concentration of the eye medication is calculated from the estimated level of receptoral blockade.

Suitably, the method further comprises the step of determining an optimal treatment regime based on the intra-ocular concentration of the eye medication.

Advantageously, the method comprises assessing whether the calculated intra-ocular concentration is in a therapeutic range.

Preferably, the method comprises determining a ratio of the calculated intra-ocular concentration to a desired intra-ocular concentration and calculating a dose or dosing frequency accordingly.

Suitably, the method further comprises the step of adjusting the dose as required.

In a preferred embodiment of the method of the invention, the medication is an anti-muscarinic medication.

Preferably, the anti-muscarinic medication is selected from the group consisting of atropine, homatropine, cyclopentolate, tropicamide, hyoscyamine and scopolamine.

Optionally, the treatment regime is a myopia treatment regime.

In one embodiment, the method further comprises the step of smoothing data with a filter.

In another embodiment, the invention further comprises the step of machine learning from the data obtained from patients.

The invention also relates to an apparatus to monitor intra-ocular penetration and/or level of receptoral action of eye medications comprising:
  a stimulation/testing chamber;
  a short wavelength visible light source configured as an adapting light, and
  a long wavelength light source as a stimulus wherein the long wavelength light source is configured to be actuatable for a duration less than or equal to the latency of eye pupil response.

Preferably, the apparatus further comprises an infra-red light source.

In a preferred embodiment, the apparatus comprises a step or impulse function to actuate the long wavelength light source for a duration less than or equal to the latency of eye pupil response.

Preferably, the apparatus comprises an infra-red detector. More preferably, the infra-red detector comprises a camera or a photodiode.

Advantageously, the apparatus further comprises a beam splitter to illuminate a retina with infra-red light from the light source along the visual axis. Preferably, the beam splitter comprises a half-silvered mirror. More preferably, the beamsplitter is co-aligned with the infra-red detector.

Preferably, the short wavelength visible light source emits light having a wavelength from about 440 nm to about 480 nm.

Preferably, the long wavelength light source emits light having a wavelength from about 550 nm to about 640 nm.

Suitably, the short wavelength visible light source is configured to be permanently on during monitoring.

In one embodiment, the light sources comprise light emitting diodes.

Preferably, the stimulation/testing chamber comprises a ganzfeld chamber. More preferably, the stimulation/testing chamber comprises a highly reflective coating to define the ganzfeld chamber.

Suitably, the stimulation/testing chamber comprises an eye-cup to receive an eye. Preferably, the eye-cup defines a light seal.

In an alternative embodiment, the apparatus comprises a Maxwellian imaging system.

Suitably, the short wavelength visible light source and the long wavelength light source are imaged into an artificial pupil.

In one embodiment, the apparatus is a monocular apparatus. Alternatively, the apparatus is a binocular apparatus.

Preferably, the apparatus further comprises a controller to control and record stimulus control, data capture, storage and analysis functions. More preferably, the controller comprises a computer.

The invention also extends to a completed implemented method of monitoring intra-ocular penetration and/or level of receptoral blockade of a medication comprising applying a short wavelength visible light and a long wavelength light to an eye wherein the long wavelength light is applied for a duration of less than or equal to the latency of eye pupil response.

Preferably, the long wavelength light is activated by a step or impulse function.

Advantageously, the long wavelength light is also applied for a duration of about twice the latency of the eye pupil response.

Preferably, the short wavelength adapting light is applied for at least two minutes.

Suitably, the long wavelength light has a wavelength of from about 550 nm to about 640 nm.

Preferably, the short wavelength visible light is activated first. More preferably, the short wavelength visible light is permanently on during monitoring.

Suitably, the short wavelength light is activated in a pulse of 200 msec or longer. Preferably, the short wavelength visible light has a wavelength of from about 440 nm to about 480 nm in order to light adapt certain classes of photoreceptors (rods and short-wavelength sensitive cones) and other photosensitive retinal cells (e.g. intrinsic photosensitive retinal ganglion cells, ipRGC).

Preferably, the invention further comprises the step of extracting a pupil diameter from a video or photosensor for each time point.

Advantageously, the method further comprises the step of smoothing data with a filter to estimate the first derivative of the pupil diameter.

In one embodiment, the invention further comprises the step of calculating at least one of the following: maximal change in pupil diameter from baseline, change at 2× latency time (approx. 400 msec) from the onset of the long wavelength stimulation light, pupil velocity at 2× latency time (approx. 400 msec), average velocity from time point=latency until 2× latency, peak velocity up to and including 2× latency time point.

Preferably, the method further comprises calculating the numerical integral of the change in pupil size from baseline to 2× latency time point.

Suitably, the method further comprises calculating the ratio of observed parameters to pre-treatment baseline values of a patient, normative age-matched data or reference group data to estimate level of functional blockade receptors within the iris.

In a preferred embodiment, the invention further comprises calculating the treatment required for a desired receptoral blockading.

Preferably, the medication is an anti-muscarinic medication. More preferably, the anti-muscarinic medication is selected from the group consisting of atropine, homatropine, cyclopentolate, tropicamide, hyoscyamine and scopolamine.

Suitably, the method further comprises the step of machine learning from the data obtained from patients.

Preferably, the method further comprises the step of varying the concentration of the medication in response to the data obtained from monitoring the intra-ocular penetration and/or level of receptoral blockade of the medication or changing the frequency of application to the eye. More preferably, the concentration of the medication is varied by adjusting the size of an eye drop containing the medication.

Most preferably, the eye drop comprises a fixed concentration eye drop having a varying viscosity. Alternatively, the concentration is varied by dynamic mixing of the medication active ingredient and a placebo.

Preferably, mixing is performed by a powered device employing a drop on demand delivery system.

Suitably, the method further comprises the step of performing a pharmacological challenge with a high dose of a suitable agonist that acts of the same receptor as the drug being tested to provide a direct assessment of receptoral blockade.

In a further embodiment, the invention also extend to a method of treating a patient with an eye medication comprising employing an apparatus as hereinbefore defined.

The invention also extends to a method of treating a patient with an eye medication comprising employing a method of monitoring intra-ocular penetration and/or level of receptoral blockade as hereinbefore defined.

In a preferred embodiment of the method of treatment, the medication is an anti-muscarinic medication.

In a further embodiment there is provided a system and computer implemented method for monitoring the level of intra-ocular concentration of an eye medication in a patient comprising:
  a testing device for testing pupil response or accommodation response to the eye medication, said device configured to test the patient to extract data on the responses of the pupil control system or accommodation control system to visual stimuli, wherein the system is configured to:
  determine the degree of action of the eye medication on the intraocular receptors in the iris and/or ciliary musculature based on the extracted data; and
  estimate the intraocular concentration of the medication based on the calculated degree of action on the intraocular receptors.

The system and method of the present invention therefore combines ocular response parameter measurement (of pupil, accommodation and/or accommodative convergence) with an algorithm optimised to estimate intraocular drug concentration from level of receptor blockade e.g. at 1% concentration in an eye drop it is possible to calculate how much binding there should be at a receptor and, by estimating the observed amount of intraocular receptor binding, the intraocular concentration and hence effective drug penetration can be calculated.

This invention therefore enables the identification of measurable aspects of the pupil and accommodation responses (which for the purposes of the present application includes accommodative convergence measurements) that can estimate receptoral blockade without being influenced by the feedback nature of the control systems involved and by other physiological factors that can influence both pupil size and accommodation. These parameters can then be integrated into a treatment method, assessment and monitoring plan to ensure that the treatment method provides optimal efficacy over time, despite any receptoral up or down regulation, with minimal side effects.

The invention therefore facilitates the estimation during treatment of the percentage of receptoral blockade at muscarinic receptors within the eye in a living subject in a clinically acceptable manner. This is particularly beneficial for the treatment of children who make up the majority of patients requiring treatment for myopic progression.

The invention facilitates the monitoring over time of any possible up-regulation of muscarinic receptors during treatment (due to irreversible receptor blockade with atropine) and any associated enhanced muscarinic response on cessation of treatment. This is of particular interest as it has been found that on cessation of treatment of myopia with high dose (e.g. 1%) atropine there is a rebound acceleration of myopia progression and eye growth. Evidence of receptor upregulation provided by the apparatus and method of the invention allows treatment to be slowly reduced to prevent rebound eye growth on cessation of therapy. Accordingly, the invention also facilitates the avoidance of rebound progression of myopia by identifying the appropriate tapering of the concentration of atropine over time once it has been deemed appropriate to cease treatment.

The systems and method of the invention can be used for patient monitoring where patients are being treated with any topical preparation that has action on the muscarinic receptors that control accommodation and/or pupil size. The device of the invention is particularly suitable for use in scenarios for which the ideal therapeutic intervention is only a partial blockade of such receptors. Examples of anti-muscarinic agents suitable for use with the invention include preparations of low dose atropine, homatropine, cyclopentolate, tropicamide, hyoscyamine and scopolamine.

There is also provided a computer program comprising program instructions for causing a computer program to carry out the above method which may be embodied on a record medium, carrier signal or read-only memory.

BRIEF DESCRIPTION OF THE DRAWINGS

The invention will now be described, by way of example only, with reference to the accompanying drawings and examples in which.

DETAILED DESCRIPTION OF THE INVENTION

The present invention enables the identification of measurable aspects of the pupil and accommodation responses that can estimate receptoral blockade without being influenced by the feedback loops of the control systems involved and by other physiological factors that can influence both pupil size and accommodation. As a result, as discussed further below, the invention provides a system for and method of monitoring/measuring the level of receptoral action and intra-ocular penetration/concentration of an anti-muscarinic medication and determining an optimal myopia treatment regime based on the level of receptoral action and intra-ocular penetration/concentration of the anti-muscarinic medication.

Figure 1:
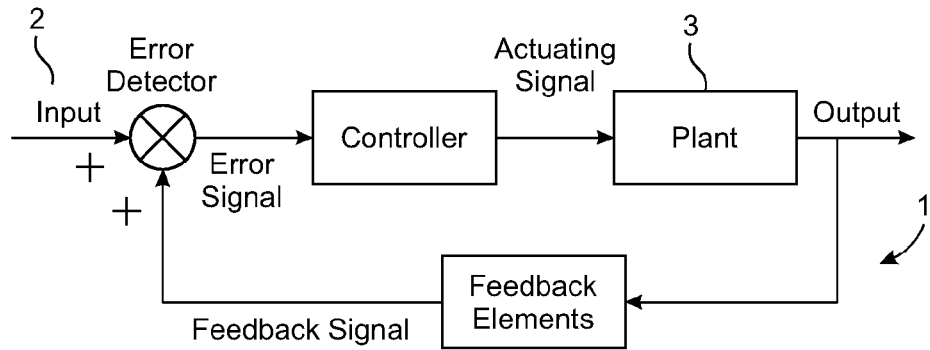
FIG. 1 is a schematic representation of the pupillary light reflex feedback loop system.

FIG. 1 shows a schematic representation of an archetypal feedback pupillary light control loop system 1 having an input 2 which for the pupillary light reflex is light intensity which is controlled in the feedback loop 1 by changes in pupil diameter and hence area. The activity that needs to be isolated in this system to estimate receptoral blockade is the plant 3, which represents the smooth muscle of the sphincter pupillae muscle and its muscarinic receptors.

Figure 2:
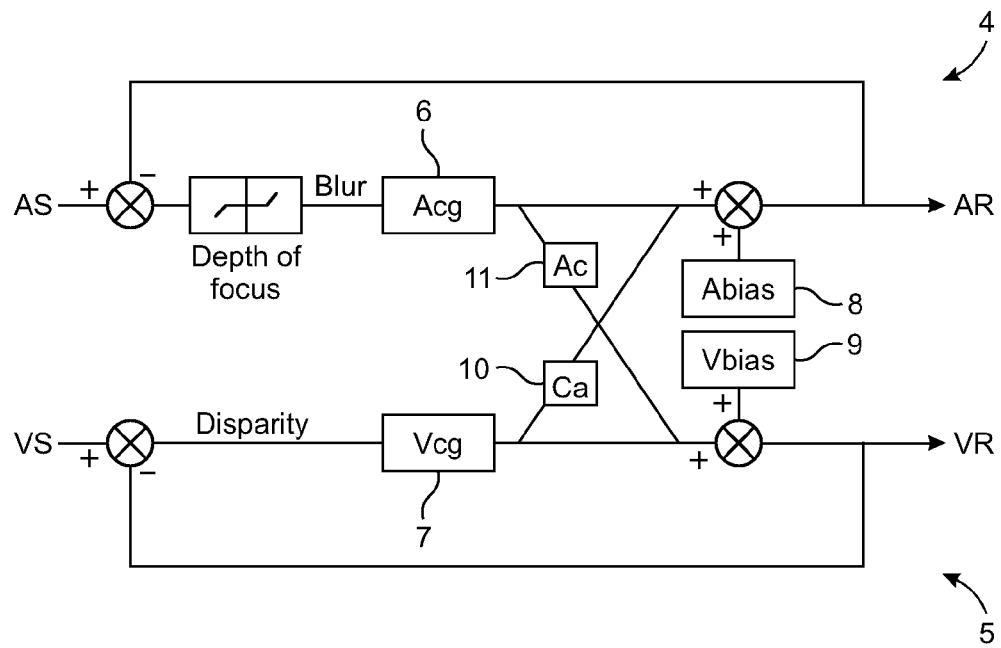
FIG. 2 is a schematic representation of the dual interacting feedback loops of accommodation and vergence where AS and VS=accommodation and vergence demand, AR and VR=accommodation and vergence response, Acg and Vcg=gains of the accommodation and vergence controllers and Abias and Vbias=resting or tonic level of accommodation and vergence, Ca=gain of convergence-accommodation crosslink and Ac=gain of accommodation-convergence crosslink.

FIG. 2 shows a schematic representation of the dual interacting feedback loops of accommodation 4 and vergence 5 where AS and VS=accommodation and vergence demand, AR and VR=accommodation and vergence response, Acg 6 and Vcg 7=gains of the accommodation and vergence controllers and Abias 8 and Vbias 9=resting or tonic level of accommodation and vergence, Ca 10=gain of convergence-accommodation crosslink and Ac 11=gain of accommodation-convergence crosslink. As shown in the drawing, the accommodation control system is even more complicated than the pupillary light reflex system 1, with interactions between the closed loop focussing system 4 and the convergence loop control system 5 which aligns the axis of the two eyes for objects at different distances. In this system, low dose antimuscarinics serve to change the accommodation response by reducing the amount of ciliary muscle contraction which leads to a change in lens shape and hence accommodation.

If the receptors involved at the level of the smooth muscle in the pupil and the ciliary body (which controls accommodation) are fully blocked (or nearly so) then no output response is observed, as is the case with full dose atropine. If only a percentage of the receptors are blocked, then the stimulus that drives the response will be reduced less effectively and less rapidly and the control mechanisms will activate for longer until the system achieves a maximal response. The feedback nature of both the pupil and accommodation control system means that the final response may only be slightly reduced even in situations where 10% or 25% of receptors are blocked.

Figure 3:
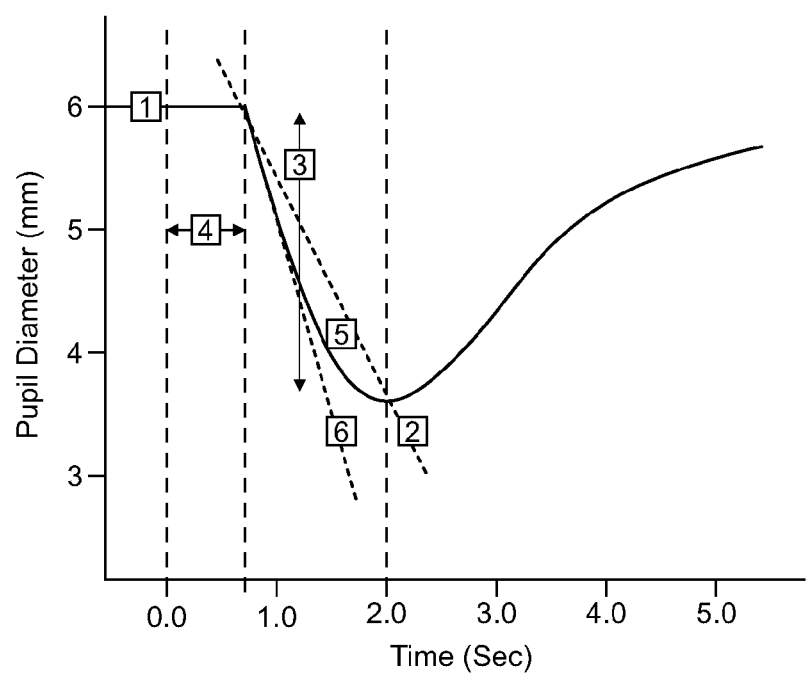
FIG. 3 is a representation of the standard parameters of the dynamic pupillary light response 1) maximal pupil diameter, 2) minimal pupil diameter, 3) pupil constriction ratio, 4) constriction latency, 5) average constriction velocity, 6) maximal constriction velocity.

As indicated above, static pupillometry measures pupil size at a given level of illumination. This is subject to diurnal variation and influenced by a range of autonomic and psychological factors as well as factors such as dietary intake of caffeine for example. FIG. 3 is a representation of the standard parameters of the dynamic pupillary light response 1) maximal pupil diameter, 2) minimal pupil diameter, 3) pupil constriction ratio, 4) constriction latency, 5) average constriction velocity, 6) maximal constriction velocity. As shown in the drawing, a range of parameters are therefore described for dynamic measures of pupil responses which measure the changes of the pupil diameter over time following the presentation of a bright light stimulus. Such measures of dynamic accommodation are rarely used in clinical practice and are generally regarded as a research tool only.

Accordingly, the known systems, devices and methods employed to measure pupil size and accommodation are only configured to monitor the functions of these in relation to either normal function or in the presence of disease rather than monitoring the level of muscarinic receptor blockade and intra-ocular penetration/concentration in the presence of anti-muscarinic medication. Accordingly, the methods and devices cannot assist in determining an optimal myopia treatment regime based on the level of receptoral action and intra-ocular penetration/concentration of anti-muscarinic medications.

As indicated above, the present invention addresses these deficiencies.

Figure 4:
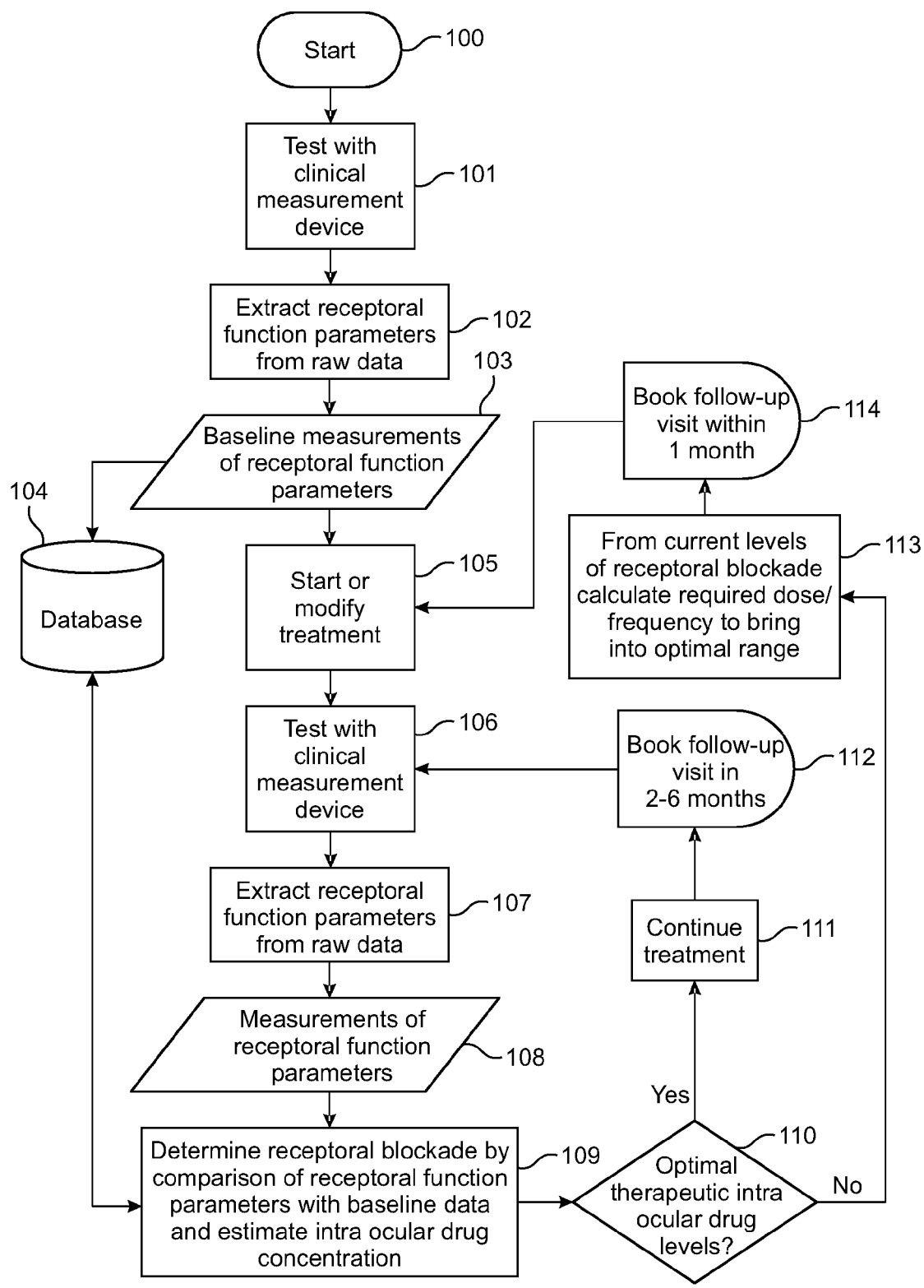
FIG. 4 is a flowchart of a first embodiment of a system for and method of monitoring/measuring the level of receptoral action and intra-ocular penetration/concentration of anti-muscarinic medications and determining an optimal myopia treatment regime based on the level of receptoral action and intra-ocular penetration/concentration of the anti-muscarinic medication.

FIG. 4 shows a flowchart of a first embodiment of a system for and method of monitoring/measuring the level of receptoral action and intra-ocular penetration/concentration of anti-muscarinic medications and determining an optimal myopia treatment regime based on the level of receptoral action and intra-ocular penetration/concentration of the anti-muscarinic medication.

As shown in the drawing, at the start 100 of the method of the invention, a patient is first tested 101 with a clinical measurement device/apparatus such as the apparatus 12 of FIGS. 7 and 8 described in more detail below. The receptoral function parameters are then extracted from raw data 102 and the baseline measurements of the receptoral function parameters obtained 103. The baseline data can include data from different eye colours, as the amount of pigment in an eye is known to influence the action of muscarinic topical medications inside the eye. The baseline measurements are then stored in a reference database 104. Treatment of the patient is then commenced 105 and the patient is then subsequently re-tested with the clinical measurement device 106 and receptoral function parameters again extracted from the raw data 107. Measurements of the receptoral function parameters are then obtained 108 and the receptoral blockade is determined 109 by comparison of Receptoral Function Parameters with the baseline data in the reference database 104 to estimate intraocular drug concentration.

An assessment is then performed of whether optimal therapeutic intraocular drug levels have been achieved 110. If optimal therapeutic intraocular drug levels have been achieved treatment is continued 111, a follow-up visit is booked (generally in 2 to 6 months) 112 for re-testing 106. If optimal therapeutic intraocular drug levels have not been achieved, from the current levels of receptoral blockade the required dose/frequency is calculated to bring the levels into the optimal range 113 (this is described in more detail in FIG. 13). A follow-up visit is then booked 114 (generally for within 1 month) for to determine whether treatment requires further modification 105.

Figure 5:
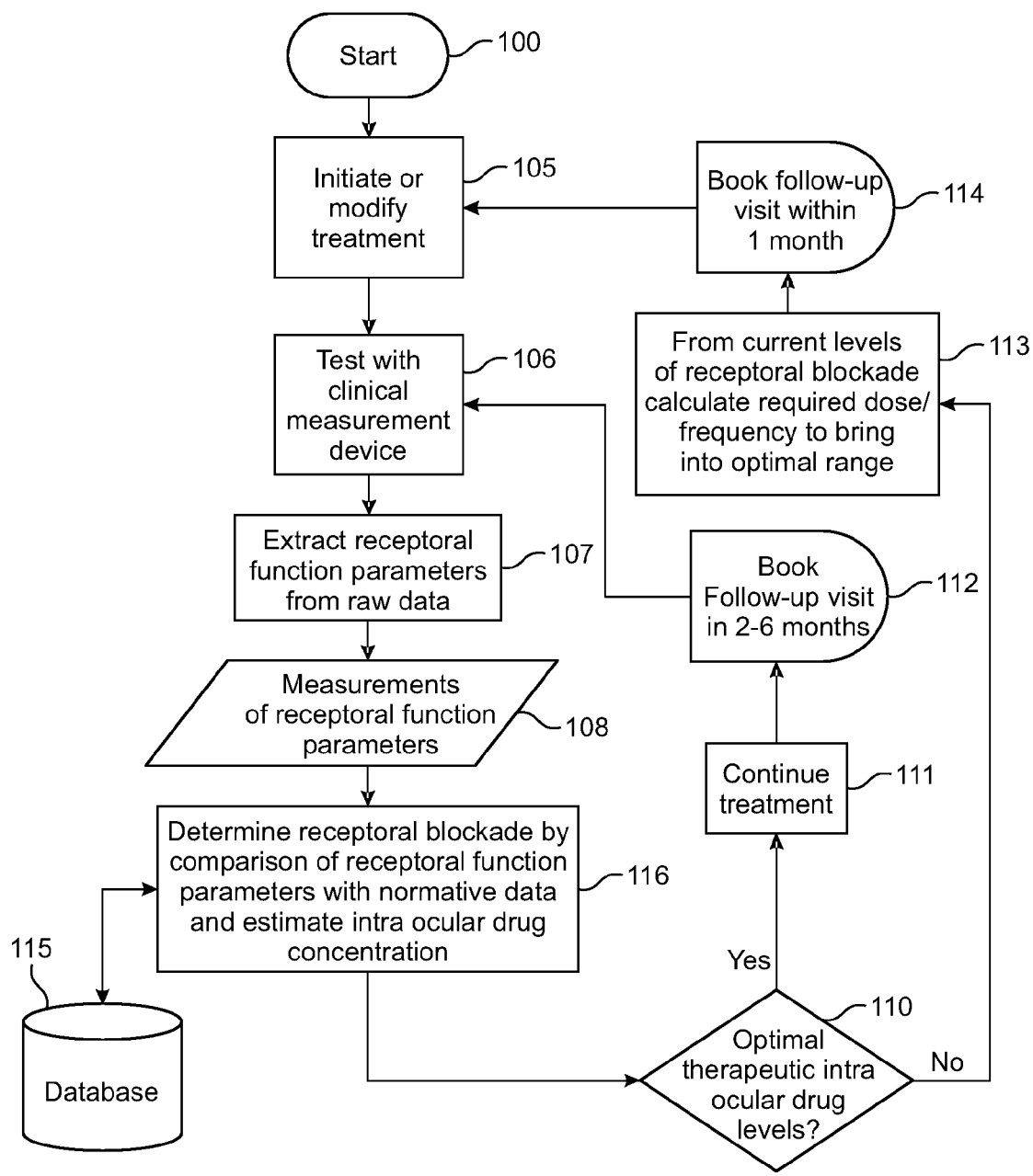
FIG. 5 is a flowchart of a second embodiment of the system and method of the invention similar to the system and method of FIG. 4 but in which a normative database is employed.

FIG. 5 is a flowchart of a second embodiment of the system and method of the invention similar to the system and method of FIG. 4 but in which a normative database is employed as the reference database. Like numerals indicate like parts. More particularly, in the present embodiment, following initiation or modification of treatment 105, testing with the clinical measurement device 106, extraction of the receptoral function parameters from raw data 106 and measurement of the receptoral functional parameters 108 a normative database 115 is employed to determine the receptoral blockade by comparison of receptoral function parameters with normative data and estimate the intraocular drug concentration 116. The optimal therapeutic drug levels are then queried 110 and subsequent actions undertaken as previously described.

In a further embodiment of the invention, the receptoral function parameters can be compared with a reference database containing reference group data i.e. trial data obtained from a reference group.

Figure 6:
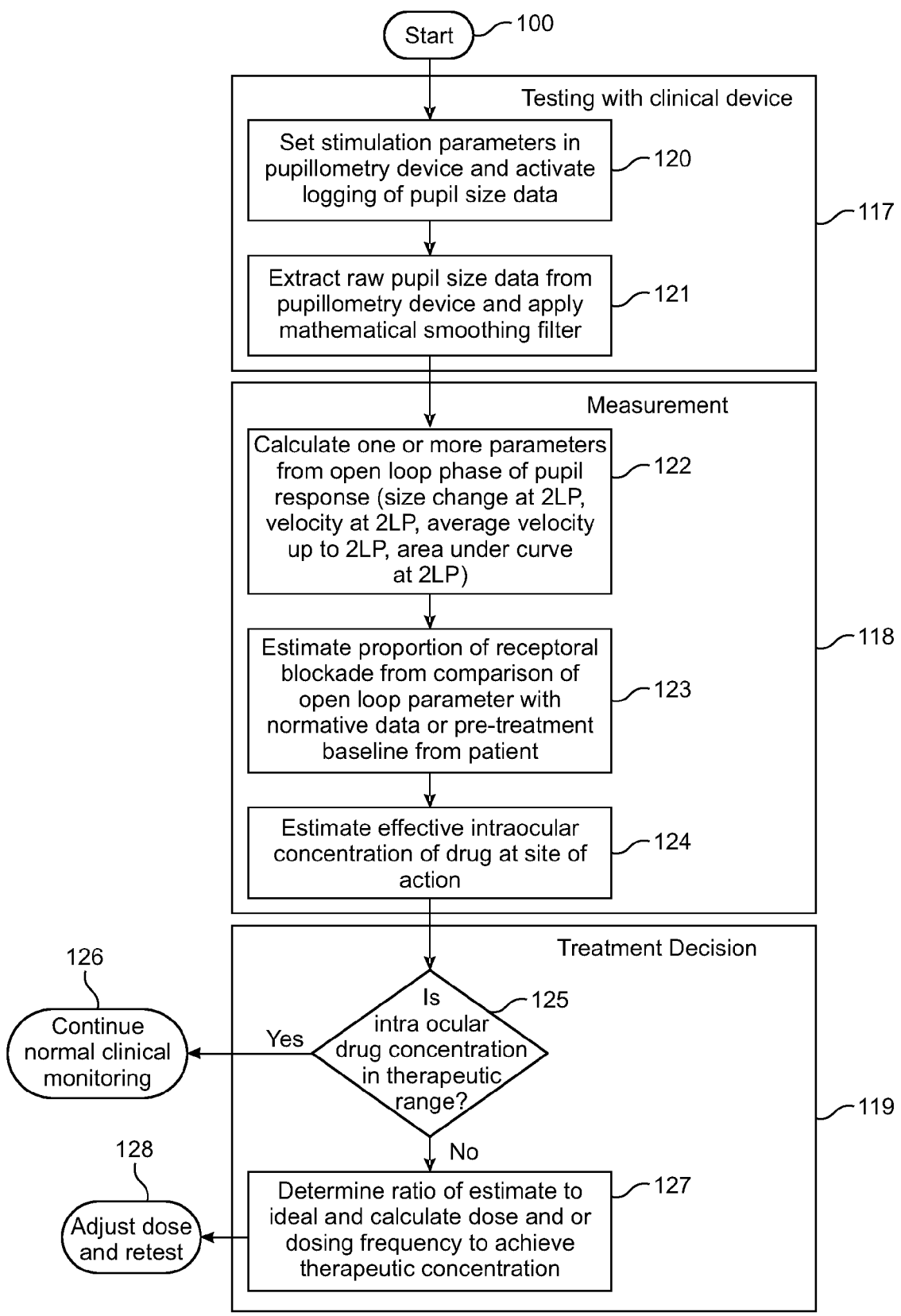
FIG. 6 is a flow chart of the data analysis performed on the data in the systems and methods of FIGS. 4 and 5 in which a measurement algorithm estimates the effective intraocular concentration of a drug at the site of action and a treatment decision algorithm determines the ratio of estimated to ideal dose and calculates the optimal dose and/or dosing frequency to achieve therapeutic concentration.

FIG. 6 shows a flow chart of the operation of the overall system and method of the invention which can be subdivided into a first step made up of testing with the clinical measurement device 117 to extract the raw test data, a second step 118 in which data analysis is performed on the data via a measurement algorithm to estimate the effective intraocular concentration of a drug at the site of action and a third step 119 in which a treatment decision algorithm is used to determine the ratio of estimated to desired/ideal dose and to calculate the optimal dose and/or dosing frequency to achieve a therapeutic concentration.

More particularly, in the first step 117 following commencement 100 of the method of the invention, the stimulation parameters are set 120 in the test measurement device and logging of the data is activated. The test measurement device can be a pupillometer, an accommodation measurement device or a method of measuring accommodative convergence as described herein. For the purposes of the present example, the test measurement device is a pupillometer such as a pupillometer as shown in FIGS. 7 and 8 and the data is pupil size data. The raw pupil size data is extracted from the pupillometer and a mathematical smoothing filter is then applied to the data 121.

The smoothed data is then subjected to the second step 118 where one or more desired parameters are calculated 122 from open the open loop phase of pupil response (e.g. size change at twice the latency period (2LP), velocity at 2LP, average velocity up to 2LP, area under curve at 2LP). The proportion of receptoral blockade is then estimated 123 from comparison of the desired open loop parameter with normative data, pre-treatment baseline from the patient or reference group data as previously described. The effective intraocular concentration of drug at site of action is then estimated 124 as outlined further below.

A treatment decision is then arrived at in the third step 119. More particularly, as outlined above, it is then queried whether the intraocular drug concentration is in the therapeutic range 125. If so, normal clinical monitoring is continued 126. If not, the ratio of estimated to ideal intra-ocular drug concentration is determined and the required dose or dosing frequency is calculated to achieve the required therapeutic concentration. The dose is then adjusted accordingly as required and the patient is retested 128.

Methodology

In the system and method of the invention, levels of receptoral blockade can be used to determine the bioavailability and effectiveness of a given preparation, compliance, and to optimise/monitor a specific patient's treatment regime, many of the steps now described can be carried out in software or a processor module configured to execute program instructions to perform one or more of the following steps. Accordingly, the system and method of the invention forms the basis of a system of monitoring drug levels in the living eye and adjusting treatment accordingly for optimal outcomes.

As shown for example in FIG. 4, a patient deemed suitable for treatment first receives a baseline assessment of pupil dynamics and/or accommodation function and/or accommodative-convergence by being tested with a clinical measurement device 101 which can be a pupillometer as described in more detail below.

Once treatment is commenced, a repeat test can be performed within a time window that allows adequate time for intra-ocular penetration (15 mins at a minimum) and at any time during the treatment phase. Follow up tests should be performed at comparable times of day, or with a similar time interval between instilling eye drops and testing of receptoral function. Baseline pupil size is also affected by ambient illumination and this should be maintained a similar level for all measurements.

For a given patient, the upper limit of tolerability of side-effects in terms of photophobia and loss of accommodation represent the maximal treatment level in terms of drug concentration or frequency of use. Where patients are finding no significant side effects (the majority of patients on low dose anti-muscarinic therapy), the degree of receptoral blockade is assessed from one or more of the oculomotor parameters which can be maximal change in pupil diameter from baseline, change at 2× latency time (approx. 400 msec), pupil velocity at 2× latency time (approx. 400 msec), average velocity from time point=latency until 2× latency and peak velocity up to and including 2× latency time point—see FIG. 6.

The concentration of the active drug can be increased by prescribing a higher concentration preparation or increasing the frequency of treatment that typically starts at once a day dosing. Conversely, if a patient is symptomatic, estimation of the level of receptoral blockade allows for prediction of an appropriate reduction in treatment.

Estimation of the receptoral blockade (see the measurements step 122 to 124 in FIG. 6) as a proportion or percentage allows for a rational adjustment of the dose, e.g. if the level of receptoral blockade is lower than the target level for optimal efficacy and minimal side effects, the concentration can be increased and then the receptoral blockade levels reassessed. Conversely where a patient is symptomatic due the impact of a preparation on pupil size and/or accommodation, the applied dose or frequency can be adjusted downwards.

The change in treatment can best estimated by a model based on the non-linear relationship between a drug's concentration and the amount of receptoral binding.

Typically, there is a sigmoidal relationship between receptor occupancy and logarithm of the drugs concentration. This can be expressed as the following equation:

$$[AR]=[A][RT]/([A]+[KA])$$

where AR is the amount of receptors bound by a drug, A is the drug concentration, KA=the apparent dissociation constant for that drug with that receptor (a well characterised value for most drugs and measured at 0.4-0.7 nM for atropine acting on human iris muscarinic receptors) and RT=the total number of receptors. This can be used to estimate the amount of bound receptors that would be obtained from the source eye drop e.g. 0.01%, 0.02% or 0.05% atropine. The same equation can be rearranged to then estimate the amount of ocular concentration/penetration from the ratio of the applied concentration to the concentration calculated from receptoral binding inside the eye.

The relationship between the receptoral blockade (expressed as a proportion from 0 to 1, i.e. percentage blockade/100) and drug concentration can be defined by the following relationships:

$$\text{Receptoral blockade } (B)=([AR]/[RT])=[A]/([A]+[KA])$$

$$\text{\& Intraocular drug concentration}=[KA]\cdot B/(1-B)$$

If the observed receptoral blockade is B, and the target proportion of receptoral blockade is $B_T$, then the ratio of required intraocular drug concentration to current drug ratio is given by:

$$\text{Ratio of required to current drug concentration}=(B_T(1-B)/(B(1-B_T))$$

Figure 13:
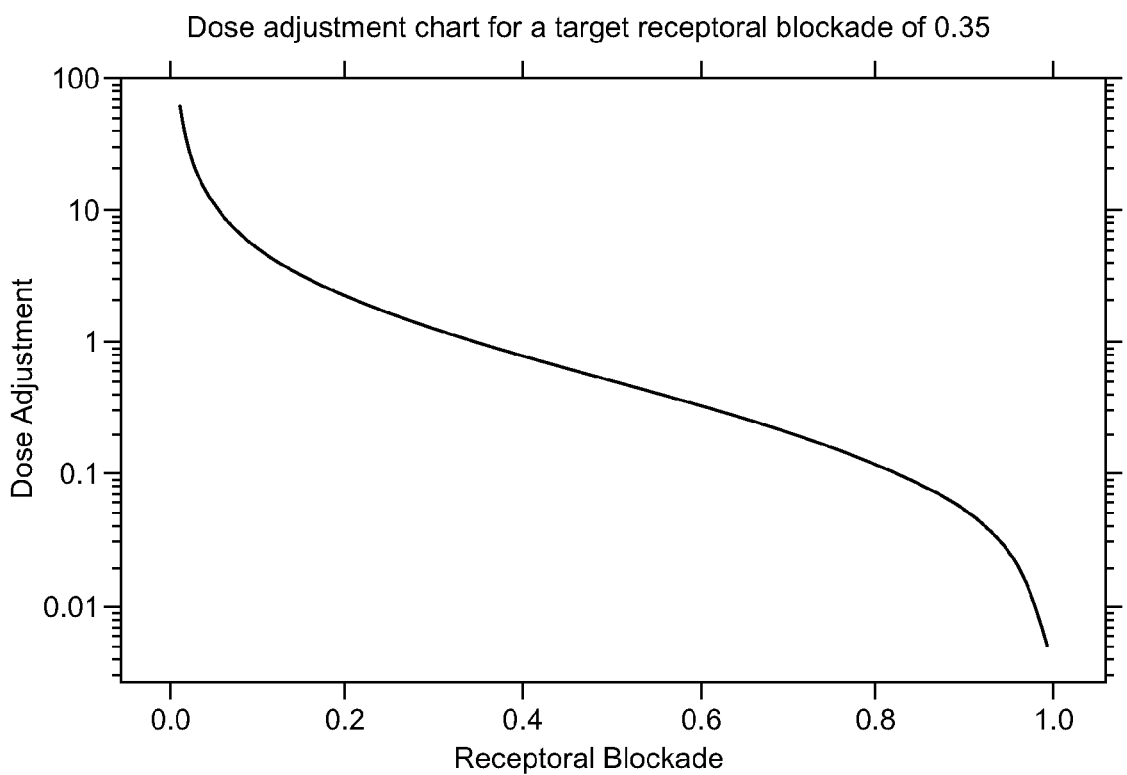
FIG. 13 is a dose adjustment chart for a target receptoral blockade of 0.35.

So if an estimated receptoral blockade of 0.1 (or 10%) is achieved and the target is 0.35 (of 35%) for optimal efficacy with minimal side effects, then the concentration in the eye should be increased by (0.35×(1−0.1))/(0.1×(1−0.35))=4.85 times. Conversely, if the initial treatment is achieving too high levels of receptoral blockade leading to side effects (e.g. 0.90 or 90%), then the appropriate concentration should be reduced to 0.06 times the original concentration to achieve a receptoral blockade of 0.35 (35%). The specific ideal target to achieve optimal myopia control for a given category of patient can be determined by a clinical trial, and then achieved in clinical practice with this invention. For a given receptoral blockade target the above equation can be plotted in graph form to provide a physical dosage adjustment calculator. As shown in FIG. 13, the observed receptoral blockade on the x-axis can be used to read off the appropriate concentration adjustment on the y-axis.

Subsequent measurements can then ensure that an adequate level of receptoral blockade is being achieved at this new treatment level to obtain the expected therapeutic effect as well as removing the experienced side effects. A very important aspect of this approach is that these adjustments can be made within a very short period following treatment initiation, allowing treatment to be optimised as early as possible. Traditionally, treatment efficacy for controlling myopia is assessed over extended periods (often over years of treatment) and it may not be recognised by a clinician that the prescribed treatment dose is ineffective until a significant length of time has passed. This is important as myopia progression is typically fast in the early stages and treatment optimisation as early as possible can facilitate maximum treatment efficacy for myopia control. Furthermore, myopia progression is generally uni-directional and the associated eye growth cannot be reversed, so a determination after 1 to 2 years of poor efficacy is 1 to 2 years of lost treatment effect that cannot be recovered. If monitoring of myopic progression over a period of 6 months or more reveals that a patient is still progressing at a fast rate, despite an apparently adequate level of receptoral blockade to minimise side-effects a decision can then rationally be made increase the treatment dosage into the range where side-effects will be expected and manage those with photochromic, varifocal glasses, or consider another form of therapy.

Treatment can also be adjusted in the absence of an individual baseline assessment by using normative data of the various parameters as described in FIG. 5.

During prolonged treatments, which is often over several years, periodic measurements will help determine if receptor up-regulation is potentially reducing the effectiveness of a preparation. On termination of treatment after a long period of time when receptor up-regulation may have occurred, increased responsiveness of the pupil light and accommodation responses may be present along with reduced accommodation-convergence responses. This presents the risk of rebound of eye growth that the original treatment was intended to reduce. In this situation, re-commencing treatment with progressive lower concentrations or less than once a day dosing can re-establish a normal level of receptoral function. Dosing concentration or frequency can then be slowly tapered over weeks or months to prevent reoccurrence of such up-regulation effects.

The above approach is based on the estimated intraocular concentration and the assumption that the dose applied at the cornea with be linearly related to that achieved intraocularly, in keeping with the observation that tear-aqueous drug transfer can be described with first-order kinetics. This has also been demonstrated to be a reasonable assumption experimentally for drugs that affect pupil size such as pilocarpine and the anti-muscarinic drug tropicamide (Yoshida S and Mishima S: A pharmacokinetic analysis of the pupil response to topical pilocarpine and tropicamide. Jpn J Ophthalmol 19:121, 1975). This assumption may, however, vary between subjects and be influenced by factors such as the amount of melanin pigment in the iris which can provide a non-receptoral binding site for anti-muscarinic drugs.

In addition, machine learning based on data obtained from patients before and after initiation of treatment with topical antimuscarinic agents can help to further refine the above algorithms. Anonymised data that include basic patient demographic information (i.e. age, race, country, gender and iris pigmentation pattern/degree), treatment history (concentration of active ingredient of eye drops and frequency of use) and the measurements of the various oculomotor parameters described above over time can be collected at different test sites and then moved to centralized, or cloud based, computer systems for further analysis to enhance treatment methods.

This data can be used in a variety of ways:
1) To enhance the accuracy of the normative, pre-treatment data and allowing better matching of a given patient to matched comparable controls;
2) To enhance the algorithms for adjustment of dosage or treatment regime according to the estimated degree of receptoral blockade, so as to ensure that if a treatment adjusted is required, the modified treatment has a higher chance of achieving the desired level of receptor blockade with a single change in treatment;
3) Once the impact of treatment has been measured in a number of patients of different ages, backgrounds and eye colours, analysis of the final optimal treatment level for a given combination of demographic features will provide recommendations of appropriate starting treatment parameters (e.g. in terms of drop concentration, drop size and frequency).

Adjustment of Intraocular Concentration of Antimuscarinic Drugs

The simplest way to achieve different intra-ocular concentrations, guided by the above systems and methods of the invention, is to vary the concentration of the active ingredient of an eye drop. As different drop concentrations will generally need to receive regulatory approval, it is likely only a small range of concentrations will be available. For atropine the range of doses currently licenced for ocular use are 1.0% and 0.5%. In addition, it is likely that additional concentrations will be made available: 0.01%, 0.02%, 0.05% and 0.1%. Drugs such as atropine have a long duration of action due to a very high receptor affinity, with effects lasting up 6-12 days. On that basis, atropine eye drops are usually given only once a day, but this is probably more frequent than necessary. This also provides another means of varying the intra-ocular concentration, namely varying the frequency of treatment.

Due to the longevity, treatment could be given less frequently than daily, with a minimum frequency of once per week for continuous action (or less for pulsed treatment regimes directed at preventing receptor up-regulation), up to an approximate upper limit of four times a day in relation to patient acceptance. Combining both approaches provides a matrix of potential treatment strategies with a limited range eye drop concentrations that provides for more flexible, and optimised treatment.

The total relative dose applied across these various options is shown below in Table 1, with once a day 0.01% atropine being the reference value of 1.0. Tables such as this can be used with the estimates of receptoral blocked from measurements of pupil responses, accommodation responses and accommodative-convergence response employing the device and methods of the invention to determine an alternative treatment regime, should the initial treatment regime not provide an appropriate level of receptor blockade to achieve both likely efficacy in myopia control and minimal side-effects.

TABLE 1

| Frequency of application | Concentration of eye drops | | | | | |
|---|---|---|---|---|---|---|
| | 1% | 0.50% | 0.10% | 0.05% | 0.02% | 0.01% |
| 1/week | 14.29 | 7.14 | 1.43 | 0.71 | 0.29 | 0.14 |
| 2/week | 28.57 | 14.29 | 2.86 | 1.43 | 0.57 | 0.29 |
| 3/week | 42.86 | 21.43 | 4.29 | 2.14 | 0.86 | 0.43 |
| 4/week | 57.14 | 28.57 | 5.71 | 2.86 | 1.14 | 0.57 |
| 5/week | 71.43 | 35.71 | 7.14 | 3.57 | 1.43 | 0.71 |
| 6/week | 85.71 | 42.86 | 8.57 | 4.29 | 1.71 | 0.86 |
| 1/day | 100 | 50 | 10 | 5 | 2 | 1 |

TABLE 1-continued

| Frequency of application | Concentration of eye drops | | | | | |
|---|---|---|---|---|---|---|
| | 1% | 0.50% | 0.10% | 0.05% | 0.02% | 0.01% |
| 2/day | 200 | 100 | 20 | 10 | 4 | 2 |
| 3/day | 300 | 150 | 30 | 15 | 6 | 3 |
| 4/day | 400 | 200 | 40 | 20 | 8 | 4 |

Employing the systems and methods described above, the impact on low dose atropine (0.01%) and another anti-muscarinic drug cyclopentolate at reduced concentration (0.05%) was evaluated in human subjects as outlined in the following Examples.

Example 1: Pupil Response Before and After Low Dose Atropine—Pupillometer

Figure 9:
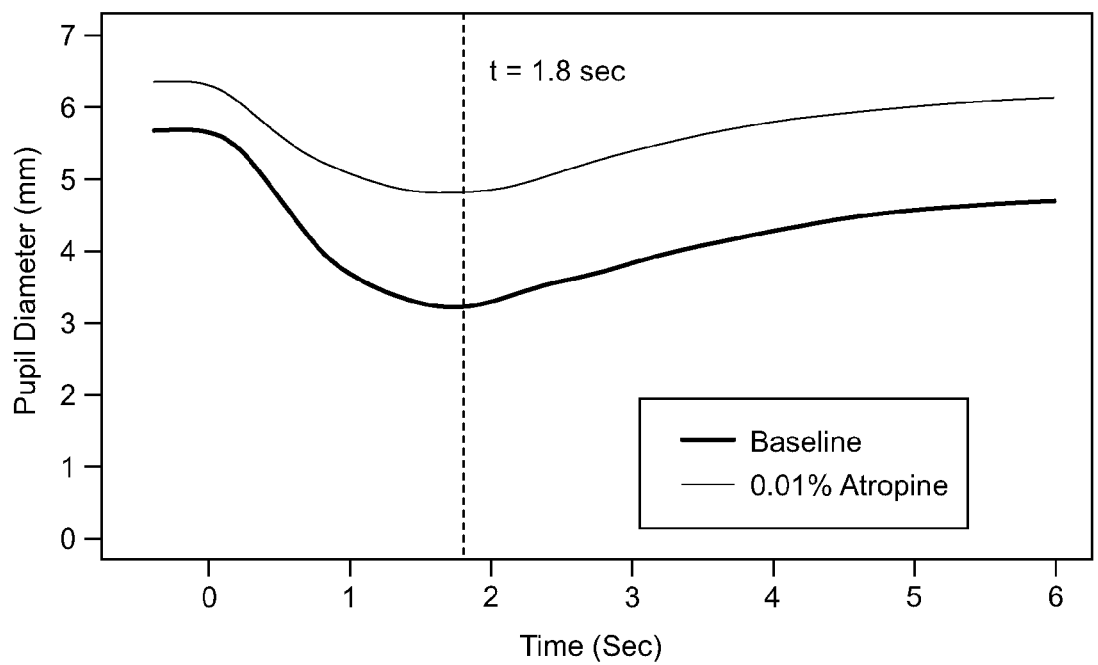
FIG. 9 is a graph of pupil response before and after low dose atropine treatment.

FIG. 9 shows dynamic pupil responses in a single subject before and a day after instillation of a diluted preparation of atropine at a concentration of 0.01%. The baseline difference in pupil size is just 0.6 mm and this subject to a range of factors, including emotional state, light adaptation and activity of the slow ipRGC system. The maximal difference in light response shows a much greater difference in the amount of pupil constriction obtained, the peak difference at 1.8 seconds being 1.6 mm, prior to a slower return to baseline. In this case the subject also showed a faster return to baseline with atropine.

Figure 10:
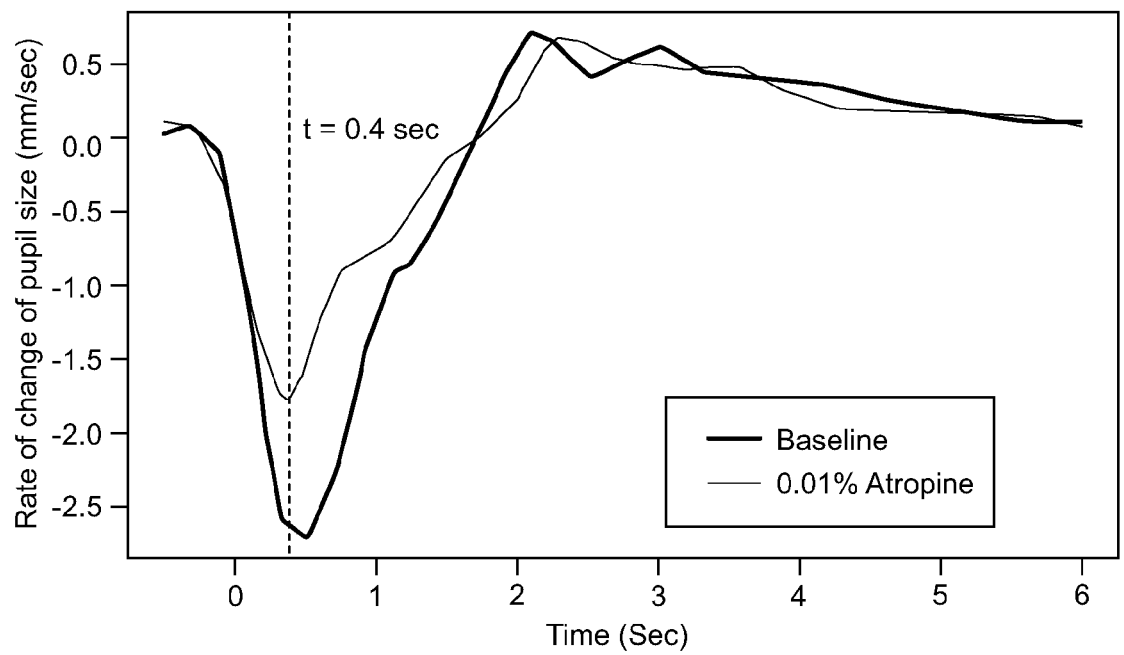
FIG. 10 is a graph of pupil constriction velocity before and after low dose atropine treatment.

FIG. 10 shows the velocity of the pupil size change, with the time point of 2× latency period (approx. 400 msec or 0.4 seconds) shown in the dotted line. The ratio of the difference in the velocity at this time point for the post- and pre-treatment response ($V400_{post}$ and $V400_{pre}$ respectively), in this case 65%, gives an indication of the degree of receptoral blockade, which is far greater than might be imagined from the small difference in baseline pupil size shown in FIG. 4. As anti-muscarinic drugs are receptor antagonists, the estimated level of receptor blockade is $1-(V400_{post}/V400_{pre})$, i.e. 35%.

Figure 11:
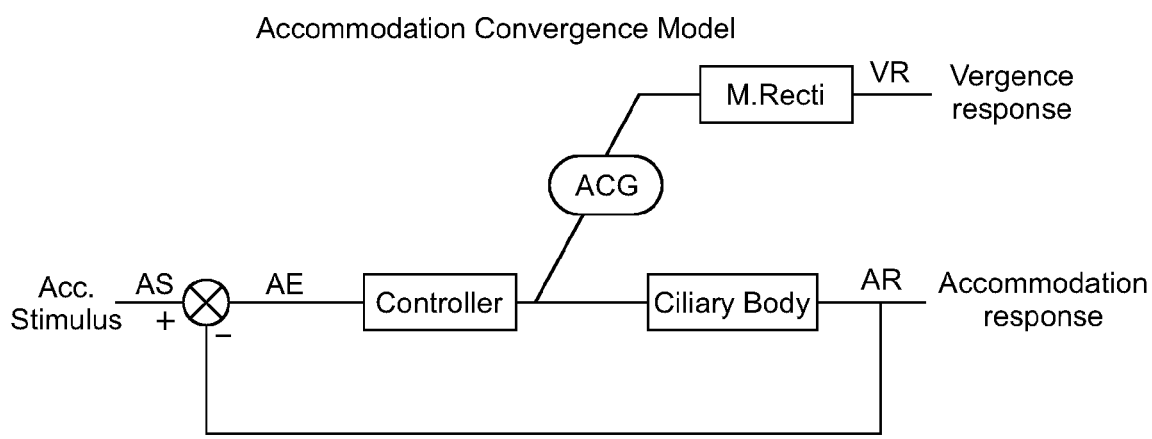
FIG. 11 is a schematic representation of an accommodation convergence control model when the convergence system is open loop.

Example 2: Accommodation Control System with Open Loop Convergence System—Accommodative Convergence FIG. 11 shows the accommodation control system when the convergence system is made open loop by covering one eye. If the response of the ciliary body is reduced by partial receptoral blockade, then the feedback nature of the accommodation response will increase the response from the accommodation control centre and result in a larger than normal signal to be sent to the ciliary body. This will partially compensate for receptoral blockade resulting in partially reduced accommodation response. This same increased internal signal is transmitted to the convergence centre which is receiving no control signal as there is no disparity cues in monocular viewing. This signal is then transmitted to the medial rectus extraocular muscles which are unaffected by the action of atropine or other anti-muscarinics to create accommodation convergence. Measuring the eye position change for a given accommodation stimulus or response allows calculation of a value called the AC/A ratio. This varies between subjects, but low dose anti-muscarinic treatment should, on the basis of control theory, lead to an increased AC/A ratio. Therefore, measuring AC/A ratio before and after treatment with low dose anti-muscarinic agents provides a mechanism for estimating the degree of receptoral blockade being achieved, and hence both the potency and the ocular penetration of the anti-muscarinic eye drop preparation being used.

The above increased AC/A ratio was demonstrated by obtaining data from 12 normal subjects with serial dilutions of cyclopentolate from 0.25% to 0.05% and measuring the AC/A (ratio of accommodation to accommodation convergence) ratios using the gradient method at 6 metres and minus lenses. They maintained the ability to accommodate sufficiently to read at 33 cm, however a mean increase in the AC/A ratio over baseline of 173% was observed. This increase results from the accommodation control system increasing the signal it is sending to the partially receptor-blocked ciliary body to achieve a comparable amount of accommodation. This increase therefore suggested a receptoral blockade of 1−100/178=0.42 or 42%.

Figure 12:
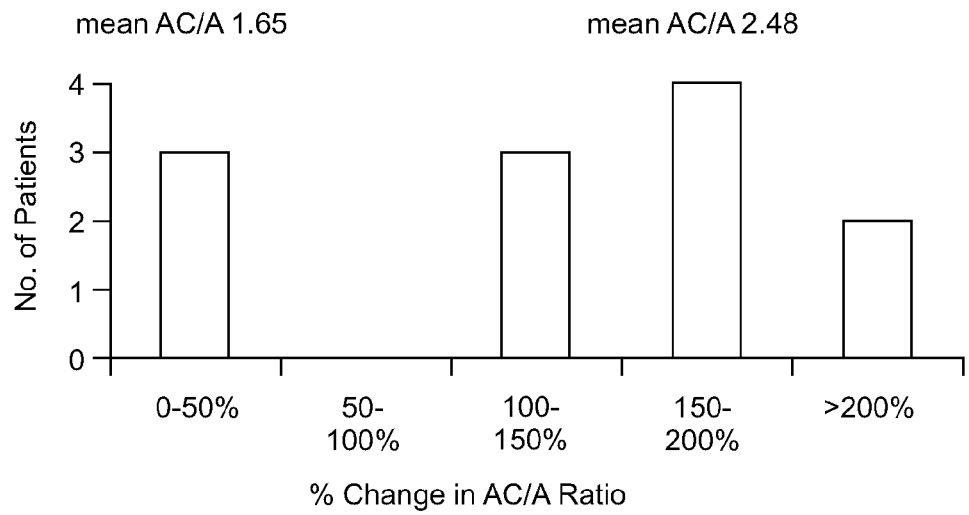
FIG. 12 is a graph of % change in AC/A ratios for different patients.

In keeping with the concept that low dose preparations may be associated with variability of response, reflecting ocular penetration due to a low gradient for drug diffusion and other issues, as shown in FIG. 12, a wide variation of changes in the AC/A ratio between subjects was observed. In this case the AC/A ratio is defined in units of metre angles/dioptre, and in these units a normal AC/A is approximately 1.0.

In relation to receptoral regulation, there is evidence that this does apply to the muscarinic receptors. Animal studies on nerve agents that inhibit acetylcholine esterase cause over-stimulation of muscarinic receptors and subsequent prolonged down regulation. Studies with the nerve agent soman (o-pinacolyl methylphosphonofluoridate) in rats (Dabisch et al 2007 TOXICOLOGICAL SCIENCES 100(1), 281-289 have shown pupil size following exposure to the agent returns to baseline within 2 days, but other aspects measures of pupillary function, including the light reflex, acetylcholinesterase activity, and pharmacological muscarinic receptor responsiveness, do not normalize for up to 10 days.

Figure 7:
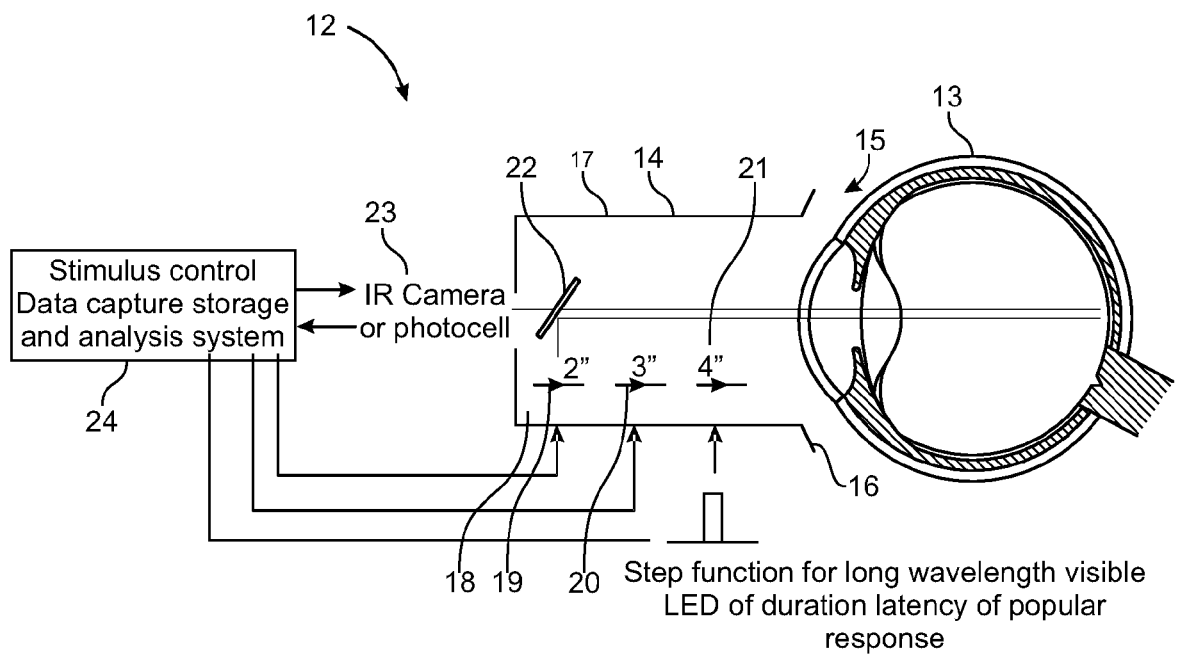
FIG. 7 is a schematic representation of a clinical measurement device/apparatus adapted to monitor intra-ocular penetration and level of receptoral blockade of topical medications disposed adjacent an eye (not to scale) using the open loop operation of the pupil light reflex.

FIG. 7 shows a schematic representation of a clinical measurement device/apparatus 12 in the form of a pupillometer 12 suitable for use in the systems and methods of the invention described above in which the pupillometer 12 uses the open loop operation of the pupil light reflex. More particularly, the clinical measuring device/apparatus 12 for monitoring intra-ocular penetration and/or level of receptoral response of eye medications in an eye 13 is generally made up of a stimulation and testing chamber 14 provided with an eye opening 15 for receiving the eye 13. The apparatus 12 can be a monocular eye-testing apparatus 12 with one chamber 14 or a binocular eye-testing apparatus with two chambers 14 so that both eyes 13 are enclosed in individual chambers 14 and the distance between the axes of the two chambers 14 is adjusted to match the interpupillary distance.

The opening 15 of the chamber 14 is provided with a soft eye cup 16 to create a light seal around the eye 13 and minimise ambient light from the environment. If a monocular apparatus 12 is employed the fellow should be covered.

Internally, the chamber 14 is provided with a white highly reflective coating 17 to create a mini-ganzfeld chamber 18. The chamber 14 is further provided with a first infra-red light source in the form of an infra-red (IR) emitting light emitting diode (LED) 19, a second short wavelength visible light source (about 440-480 nm) 20 in the form of a short wavelength visible light emitting LED and a third long wavelength light source (about 550-640 nm) 21 in the form of a long wavelength light emitting LED.

The chamber 14 is further provided with a beam splitter 22 which can be a half-silvered mirror to ensure that IR light illuminates the retina along the visual axis.

Externally, the apparatus 12 is provided with an IR detector 23 in the form of an IR camera or photocell/photodiode 23. An infra-red filter (not shown) is disposed in front of the IR camera or photocell/photodiode 23.

The apparatus is controlled by a controller 24, which can be a computer, which controls and record stimulus control, data capture, storage and analysis functions. Importantly, the apparatus 12 has a step function 25 for long wavelength visible LED 21 activation of a duration less than or equal to the latency of pupil response.

The apparatus 12 is operated by placing the eye 13 against the eye opening 15 in the stimulation and testing chamber 14 at the soft eye cup 16. The IR emitting LED 19 emits invisible infra-red light that is directed into the pupil and then imaged back to the IR camera or photocell/photodiode 23. The IR filter in front of the camera excludes visible light emitting from the short wavelength emitting and long wavelength emitting LEDs 20,21.

The short wavelength visible light emitting LED 20 is permanently on during testing. This light inactivates the rods and short wavelength sensitive cones (s-cones) by light adaptation and provides a stable baseline stimulation of ipRGC's. This minimises the impact of variable prior light adaptation and eliminates three of the five light dependent inputs to the pupil response (rods, SWS cones and ipRGCs). The reflective coating 17 of the testing chamber 14 ensures that the adapting light from the short wavelength visible light emitting LED 20 reaches all retinal areas within the eye 13 to maximise light adaptation of the rods.

The long wavelength light emitting LED 21 emits long wavelength light (550-640 nm) to preferentially stimulate long wavelength and medium wavelength sensitive cones. During testing the long wavelength light emitting LED 21 is activated by an impulse function to illuminate the eye 13 for a period equal to the latency of the pupil light e.g. approximately 200 msec or up to twice the latency period (400 msec). The short latency is a critical feature to isolate the feedback loop aspect of the pupillary light reflex and other more complex temporal features. The reflective coating 17 of the testing chamber 14 ensures that the adapting light from this LED 21 reaches all retinal areas within the eye to maximise the response.

The beamsplitter or half silvered mirror 22 ensures that the IR light illuminates the retina along the visual axis and is co-aligned with the IR camera or photocell/photodiode detector 23 to ensure that the whole of the pupil area is illuminated to enhance video analysis or pupil size calculation from the total amount of reflected IR light.

Whereas a standard pupillometer aims to determine the overall response of the system from both a sensory and motor aspect, the apparatus 12 is configured to eliminate many variable sensory inputs, many non-sensory bias effects on pupil size and many aspects of the overall control system and feedback loop in order to estimate the level of function at the nerve-muscle interface of the iris sphincter muscle that causes pupil constriction.

Figure 8:
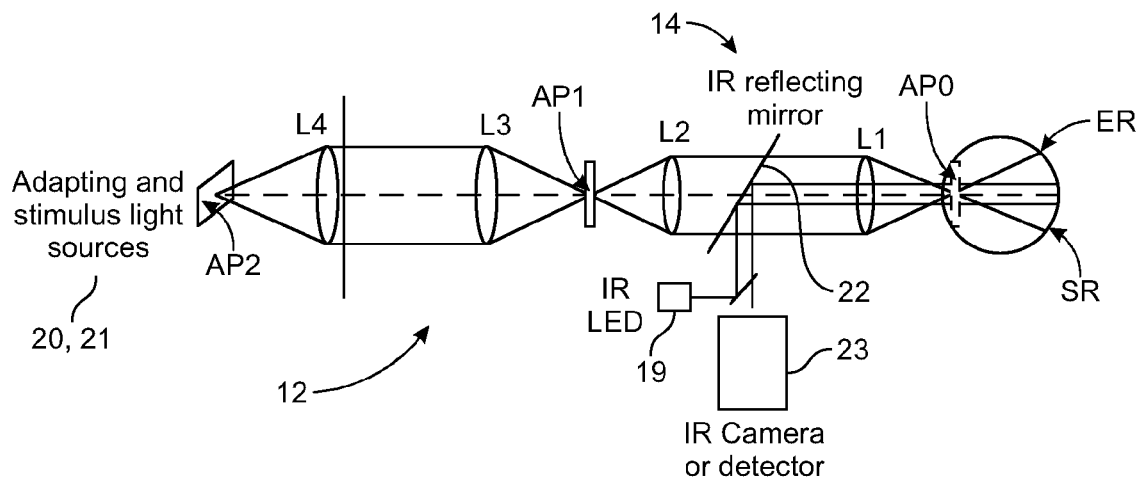
FIG. 8 is a schematic representation of an alternative embodiment of the clinical measurement device in which a Maxwellian imaging system is employed.

FIG. 8 is a schematic representation of an alternative embodiment of the apparatus 12 of the invention in which a Maxwellian imaging system is employed. Like numerals indicate like parts. As shown in the drawing, in this apparatus 12 the adapting and stimulus sources at AP2 are imaged into an artificial pupil (AP1) by two lenses (L4 and L3). This light source is then projected into the pupil plane (AP0) of the eye by lenses L2 and L1. Provided the projected aperture is larger than the pupil size, the system will operate in an open loop fashion to light stimulation, as the pupil constriction will not alter the amount of light entering the eye. To maximise pupil size, in this configuration the adapting light source can be turned off shortly before the stimulus light source is activated. The pulse length in this configuration is not critical to measuring open loop function and hence can be increased if needed to obtain more robust pupil responses.

The apparatus 12 is a monocular or binocular testing apparatus 12 for measuring pupil size and recording changes of pupil over time with a temporal resolution (sampling rate) of at least 20 Hz and preferably 50-100 Hz. The faster the sampling rate the greater the resulting temporal resolution. During testing, the short wavelength (about 440-480 nm) adapting light 20 of at least 30 cd/m$^2$ and the testing light 21 of long wavelength (at least about 550 nm up to 650 nm) operate. As indicated above, these can be implemented in the form of light emitting diodes 20,21 with appropriate diffusers.

The short wavelength adapting light 20 acts to minimise the influence of rods, short wavelength sensitive cones (s-cone) and ipRGCs (intrinsically photosensitive retinal ganglion cells) which normally contribute to the pupillary response. Although a normal part of the pupil response, in this device their input is unhelpful as the ipRGC response is very slow and prolonged and the rod contribution is very sensitive to prior light adaptation. The variable state of rod adaptation provides a significant source of variation in pupillary light response. It takes up to 30 mins in the dark to fully restore rod function, but 2-10 mins in a short wavelength adapting light and they can be effectively suppressed. It is therefore preferable to suppress the rods and measure the medium- and long wavelength sensitive (m-cone and l-cone) cone-derived pupil light response to remove this source of sensory variability to pupil testing. The m-cone and l-cone driven response is also generally faster and more transient than the rod and ipRGC driven response and hence a better measure of the activity of receptors in the pupillary muscle fibres. The long wavelength test light 21 preferentially stimulates middle- and long-wave sensitive cones, and has minimal impact on any residual functioning rods or ipRGC's. This provides additional isolation of the m-cone and l-cone responses. The test protocol involves the adapting light 20 being activated first, and then a short pulse of the long wavelength testing light 21 to stimulate the pupillary light response.

As discussed above, the feedback nature of the pupillary light reflex complicates assessment of the degree of receptoral blockade. To get an assessment of the pupil light response without the feedback loop influencing the result, the simplest approach is to have a pulse of the long wavelength testing light 21 which is the same duration as the latency of the pupil light response (170-220 msec approximately). In this way the stimulus has been removed before the pupil can start to respond. The apparatus 12 is therefore operating in an open loop manner, entirely unaffected by the feedback loop. At a time period of twice the latency period (2LP, which corresponds to 340-440 msec), the pupil control system of the eye will effectively stop responding to the stimulus, and this is the optimal time to determine the response parameters of the pupil in order to estimate the degree of receptoral blockade. At this 2LP timepoint the change in pupil size from base line, the velocity of pupil constriction at this point and the integral of the change in pupil size during the time interval of stimulus onset+latency time and stimulus onset+2× latency time. The peak constriction will typically occur later than this time point, but as the system is operating in an open loop fashion this parameter can also be used.

If longer pulses are used, such as a 1 sec pulse to ensure a large pupil response, the system is responding in an open loop manner for a time period equal to twice the latency of the pupillary light reflex, i.e. 340 msec-440 msec. The pupil will start to constrict at 170-220 msec, but the impact of that constriction as part of the feedback loop isn't apparent until another latency period has expired, hence the threshold of 2× the latency period (2LP). At this 2LP timepoint the change in pupil size from base line, the velocity of pupil constriction at this point and the integral of the change in pupil size during the time interval of stimulus onset+latency time and stimulus onset+2×latency time represent the open-loop component of the pupil response.

An alternative approach is to use the more complicated Maxwellian view optical system shown in FIG. 8 to deliver the light to the eye 13 through a fixed artificial pupil imaged into the pupil plane, which is smaller than the patient's natural pupil. In this case the pupil response will be unaffected by the feedback loop as pupil constriction will not reduce the amount of light entering the pupil provided the pupil remains larger than the projected pupil.

The device 12, or device-computer combination calculates the necessary parameters of the pupil response from the sequence of measurements of pupil size over time. Pupil responses can be measured either monocularly or binocularly for this purpose. Estimation of the degree of blockade of the muscarinic receptors in the front of the eye is obtained by comparing one or more of the above parameters (i.e. velocity at 2LP time-point, change in diameter at 2LP and the integral of the change of pupil size from time (t)=latency to t=2× latency) when the patient is on treatment to the same patient's pre-treatment response, or to a normative database or to reference. The ratio of the parameter on treatment to the baseline expressed, for example, as a percentage provides the simplest metric. Allowing for some measurement variability, the average of the ratio of several parameters will provide more reliability, as will an average of repeated measures.

An additional feature of the apparatus 12 is the addition of components to measure the ocular accommodation response to changes in stimulus vergence. For measurement of accommodation the same principles apply, but the accommodation system has a slower initial response latency of 300 to 400 ms. For the application of estimating muscarinic blockade presenting small step changes in stimulus vergence (1-2 dioptres) are preferable to large changes in stimulus vergence. Within the device the stimulus to accommodation is ideally provided by a fixation target with sufficient spatial detail to provide a good focusing target. The target can be imaged with a Badal lens system, allowing the fixation target to be rapidly moved by a stepping motor to achieve the change in stimulus. The comparable accommodation parameters to those used to determine the impact of an antimuscarinic preparation on pupil responses are of interest: notably the velocity of accommodation change at twice the latency period (600-800 msec), the amplitude of the change and the integral of the accommodation change during the time (t)=latency to t=2× latency. Accommodation responses can be measured either monocularly or binocularly for this purpose.

The Badal stepping motor system used to stimulate the accommodation system can also be used in monocular viewing to stimulate the accommodation-convergence response, with the accommodation-convergence being measured by the convergent movement of the non-viewing eye while the viewing eye remains fixed on the fixation target. Eye position can be measured by a variety of means including a limbal tracker or video analysis or corneal reflex position in relation to the pupil or limbus. The accommodation-convergence response can be defined in terms of degrees of prism dioptres/per dioptre of accommodation stimulus change (via the Badal lens stimulation system) or per dioptre of accommodation.

The testing sequence performed by the apparatus 12 can therefore be summarised as follows:

1) Cover other eye in monocular testing device;
2) Place observer's eye in position in the device;
3) Activate the long wavelength adapting LED 21 for at least 2 minutes;
4) Start collecting continuous samples of video or amount of IR light reflecting from pupil at high sampling rate (>25 Hz) from at least 1 second prior to light stimulus to obtain baseline;
5) Activate the stimulus short wavelength LED 20 in a pulse of 200 msec or longer, and
6) Extract pupil diameter from video or photosensor for each time point.

The data from the apparatus can then subjected to the process steps previously outlined in FIGS. 4 to 6 as follows:

7) Smooth data with a filter to estimate the first derivative of the data extracted in step 6, i.e. pupil size change velocity;
8) Calculate at least one of the following: maximal change in pupil diameter from baseline, change at 2× latency time (approx. 400 msec), pupil velocity at 2× latency time (approx. 400 msec), average velocity from time point=latency until 2× latency, peak velocity up to and including 2× latency time point. Calculate the numerical integral of the change in pupil size from baseline to 2× latency time point.
9) Calculate ratio of observed parameters to pre-treatment baseline values of that patient, normative age-matched data or reference group data to estimate level of functional blockade of the muscarinic receptors within the Iris.
10) Determine the intraocular concentration of the drug at the receptors from the level of functional blockade of the muscarinic receptors and the receptor binding properties of the drug.
11) Determine whether the current treatment is producing a therapeutic intraocular concentration of the drug.
12) If not, calculate the dosage adjustment required to bring the intraocular concentration of the drug into the therapeutic range.

The device 12 can either contain a micro-processor unit to store and provide numerical analysis of the pupil light responses obtained, or be connected to a general purpose computer for this purpose. The device 12 may also be incorporated, as a sub-component, to a comprehensive ocular measurement devices such as those that measure axial length, corneal curvature and refraction to provide a single device suitable for management of all aspects of clinical myopia control.

As indicated above, the devices 12 of FIGS. 7 and 8 are exemplary devices only and it is to be noted that the testing device 12 employed in the method and system of the invention can be any clinical measurement device which is capable of measuring pupillary light responses and/or accommodation and/or accommodation-convergence and is adapted to minimise sensory factors and feedback control system features that might influence these responses. The use of such devices in the systems and methods of the invention are hereinbefore described.

More refined ways for controlling treatment regime can be employed in order to optimise treatment. Other parameters include the size of the eye drop. Due to the limited size of the tear film and capacity of the lower fornix of the eye (6-8 microlitres) to hold an eye drop, drop size is not a very effective way of varying the amount absorbed by the eye. Standard drops contain approximately 25-50 microlitres of solution and the excess over what the inferior fornix can retain is drained out of the nasolacrimal duct or falls out of the eye. For standard sized eye drops, viscosity has a significant impact on intraocular absorption by increasing contact time of the drop with the eye. A fixed concentration eye drop with varying viscosity could therefore also be used to achieve different intraocular concentrations.

Alternative approaches to controlling the concentration include dynamic mixing of the active ingredient and a placebo preparation without the active ingredient, but otherwise identical, as is usually used in clinical trials. A preparation of 0.1% atropine combined a with a placebo, could provide a wide range of clinically relevant concentrations with two preparations for which clinical trial data would be available.

Usually the placebo would not be marketed as a product, but in this case the placebo is used as a diluent which will already have been subject to similar safety and tolerability studies to the active compound within regulatory trials. The mixing of the two preparations could be achieved at a dispensing level, providing a bottle with the required concentration by mixing the two approved preparations active drug and placebo in the required proportions, or achieved within a dispensing device containing two reservoirs of active and placebo that releases a mixture of the two preparations. The ratio of the two could be defined by physical parameters such as delivery nozzle fed by tubes of differing diameters. A standardized dual reservoir eye drop bottle could also be fitted with a range of different delivery nozzles that contain two delivery tubes of the same or differing diameters. For example, this device could provide flow controlled dilution from the two reservoirs with a 1:1 dilution for 0.05%, or 1:3 (drug:placebo) for 0.025% or 1:5 for 0.017%.

Alternative approaches for mixing could involve powered devices that employ drop on demand delivery systems as currently used in inkjet printers. There are two mechanisms that would be suitable thermal drop on demand systems for drugs/placebo preparations that are temperature stable and piezoelectric drop on demand for temperature sensitive preparations. Two parallel delivery systems would be required to deliver a configurable amount of active and placebo diluent to the eye surface. Such a delivery device would be analogous to a configurable insulin injection device, where a single preparation is delivered.

Drop on demand technology can provide for smaller and configurable volumes than conventional eye drop delivery devices (e.g. 8 microlitres), but using volumes comparable to the existing tear-film volume (6-8 microlitres) provides for similar drug absorption into the eye as much larger conventional eye drops with the same concentration of active drug, albeit with less systemic absorption (Ianchulev, T., Weinreb, R., Tsai, J. C., Lin, S., & Pasquale, L. R. High-precision piezo-ejection ocular microdosing: Phase II study on local and systemic effects of topical phenylephrine. Therapeutic Delivery, 2018, 9(1), 17-27). Therefore, to achieve different levels of drug activity within the eye, micro-dosed volumes should range from 1 to 8 microlitres. This could provide for customized treatments from a small range of approved eye drop concentrations.

The conjunctival surface is relatively insensitive compared to the highly sensitive cornea surface. Accordingly, this also provides a mechanism for highly controlled drug delivery via contact devices that can deliver drugs through the conjunctival surface with iontophoresis, whereby drugs are molecules are transported across epithelial surfaces by electrophoresis and electroosmosis. The delivery concentration depends on source concentration of the preparation, surface area of the delivery system, duration of the application and electrical potential. Several other existing technologies could also be used to delivery ocular drugs these include microfluidic ion pumps.

In an alternative application of the device and methods of the invention, in addition to monitoring the effect of just the low dose antimuscarinic alone, a pharmacological challenge can also be performed and measured with the device described to provide a more direct assessment of receptoral blockade. This approach can also be used to calibrate the relationship between the oculomotor parameters measured with the device of the invention and receptoral blockade in a given clinical population.

For example, to assess the degree of pharmacological blockade, the response of the pupil or accommodation system to topically applied muscarinic agonists at concentrations sufficient to achieve a maximal physiological response by a high level of receptor binding is measured. Such agents include pilocarpine and oxotremorine. These drugs will normally induce an intense pupil constriction (miosis). This action will be reduced in proportion to the amount of receptoral blockade induced by a low dose muscarinic antagonist such as low dose atropine. The degree to which the pupil response and accommodation response, as measured with this device, to muscarinic agonists are attenuated by a low dose antimuscarinic provides a direct estimate of receptoral blockade.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. a memory stick or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention claimed is:

1. A system for monitoring the level of intra-ocular concentration of an anti-muscarinic eye medication in a patient comprising:
   a testing device for testing pupil response or accommodation response to the anti-muscarinic eye medication, said device configured to test the patient to extract data on the pupil response or accommodation response, and the system is configured to:

estimate the intraocular concentration of the anti-muscarinic medication based on the extracted data, wherein the intraocular concentration is estimated by computing at least one data parameter value from the extracted data and comparing with a reference database of known data parameters and the at least one data parameter comprises maximal change in pupil diameter from baseline, size change at 2× latency time, pupil velocity at 2× latency time, average velocity up to 2× latency time, peak velocity up to and including 2× latency time point and area under curve at 2LP, an accommodation or accommodative convergence parameter.

2. A system as claimed in claim 1 wherein a level of receptoral blockade caused by the eye medication is estimated by comparing the at least one data parameter value with a reference database comprising a pre-treatment patient baseline.

3. A system as claimed in claim 2 wherein the level of intraocular concentration of the anti-muscarinic eye medication is calculated from the estimated level of receptoral blockade.

4. A system as claimed in claim 3 further comprising the step of determining an optimal treatment regime based on the intra-ocular concentration of the eye medication and/or assessing whether the calculated intraocular concentration is in a therapeutic range.

5. A system as claimed in claim 4 comprising determining a ratio of the calculated intra-ocular concentration to a desired intraocular concentration and calculating a dose or dosing frequency accordingly.

6. A system as claimed in claim 4 wherein the treatment regime is a myopia treatment regime.

7. A system as claimed in claim 1 wherein the at least one data parameter comprises a pupil size or pupil response latency or pupil constriction speed.

8. A method of treating a patient with an anti-muscarinic eye medication comprising:

testing the patient to extract data on the pupil response and/or accommodation response, and estimating the intraocular concentration of the anti-muscarinic eye medication based on the extracted data to monitor the level of intra-ocular concentration of the anti-muscarinic eye medication in the patient, wherein the intraocular concentration is estimated by computing at least one data parameter value and comparing with a reference database of known data parameters and the at least one data parameter comprises maximal change in pupil diameter from baseline, size change at 2× latency time, pupil velocity at 2× latency time, average velocity up to 2× latency time, peak velocity up to and including 2× latency time point and area under curve at 2LP, an accommodation or accommodative convergence parameter.

9. A method as claimed in claim 8 wherein a level of receptoral blockade caused by the anti-muscarinic eye medication is estimated by comparing the at least one data parameter with a reference database comprising a pre-treatment patient baseline.

10. A method as claimed in claim 9 wherein the level of intra-ocular concentration of the anti-muscarinic eye medication is calculated from the estimated level of receptoral blockade.

11. A method as claimed in claim 10 further comprising the step of determining an optimal treatment regime based on the intra-ocular concentration of the anti-muscarinic eye medication and/or assessing whether the calculated intra-ocular concentration is in a therapeutic range.

12. A method as claimed in claim 11 comprising determining a ratio of the calculated intraocular concentration to a desired intra-ocular concentration and calculating a dose or dosing frequency accordingly.

13. A method as claimed in claim 8 wherein a level of receptoral blockade caused by the anti-muscarinic eye medication is estimated by comparing the at least one data parameter with a reference database comprising a normative database or reference group data.

14. A method as claimed in claim 8 wherein the at least one data parameter comprises a pupil size or pupil response latency or pupil constriction speed.

* * * * *